(12) United States Patent
Thomas et al.

(10) Patent No.: US 11,471,837 B2
(45) Date of Patent: Oct. 18, 2022

(54) SELF-PRESERVING BIODEGRADABLE ENVIRONMENTAL DNA FILTER

(71) Applicants: Austen Clouse Thomas, Kalama, WA (US); Jesse Andrew Howard, Vancouver, WA (US)

(72) Inventors: Austen Clouse Thomas, Kalama, WA (US); Jesse Andrew Howard, Vancouver, WA (US)

(73) Assignee: Smith-Root, Inc., Vancouver, WA (US)

( * ) Notice: Subject to any disclaimer, the term of this patent is extended or adjusted under 35 U.S.C. 154(b) by 510 days.

(21) Appl. No.: 16/780,816

(22) Filed: Feb. 3, 2020

(65) Prior Publication Data

US 2020/0246755 A1 Aug. 6, 2020

Related U.S. Application Data

(60) Provisional application No. 62/800,248, filed on Feb. 1, 2019.

(51) Int. Cl.
*B01D 67/00* (2006.01)
*C12Q 1/6806* (2018.01)
(Continued)

(52) U.S. Cl.
CPC ....... *B01D 67/0088* (2013.01); *B01D 63/087* (2013.01); *B01D 67/0093* (2013.01);
(Continued)

(58) Field of Classification Search
CPC .............. B01D 67/0088; B01D 63/087; B01D 67/0093; B01D 2315/08; B01D 2325/36; B01D 61/14; B01D 69/12; C12N 15/1017; C12Q 1/6806; G01N 1/14; G01N 1/4005; G01N 2001/1025; G01N 2001/4088; G01N 1/405
See application file for complete search history.

(56) References Cited

U.S. PATENT DOCUMENTS 5,004,543 A   4/1991  Pluskal
8,920,339 B2 12/2014  Mao
(Continued)

OTHER PUBLICATIONS

Carim, K. J., T. Padgett-Stewart, T. M. Wilcox, M.K. Young, K.S. McKelvey, and M.K. Schwartz. (2015) Protocol for collecting eDNA samples from streams. U.S.D.A. Forest Service, National Genomics Center for Wildlife and Fish Conservation. V2.3 (Jul. 2015).

(Continued)

*Primary Examiner* — Jennifer Wecker
*Assistant Examiner* — Jonathan Bortoli
(74) *Attorney, Agent, or Firm* — J. Curtis Edmondson; Law Offices of J. Curtis Edmondson

(57) ABSTRACT

An inline filter housing with a biodegradable, hydrophilic material that operates in conjunction with a field sampling apparatus to both concentrate field sampled environmental DNA particles from water samples and to automatically preserve the captured DNA via desiccation, thus avoiding filter membrane transfer steps, chemicals or cold storage preservation requirements. The hydrophilic filter housing is capable of rapidly preserving the field sampled environmental DNA captured on the filter membrane at ambient field temperatures.

20 Claims, 8 Drawing Sheets

(51) Int. Cl.
   *G01N 1/14* (2006.01)
   *G01N 1/40* (2006.01)
   *B01D 63/08* (2006.01)
   *C12N 15/10* (2006.01)
   *G01N 1/10* (2006.01)

(52) U.S. Cl.
   CPC ....... *C12N 15/1017* (2013.01); *C12Q 1/6806* (2013.01); *G01N 1/14* (2013.01); *G01N 1/4005* (2013.01); *B01D 2315/08* (2013.01); *B01D 2325/36* (2013.01); *G01N 2001/1025* (2013.01); *G01N 2001/4088* (2013.01)

(56) References Cited

U.S. PATENT DOCUMENTS

| | | | | |
|---|---|---|---|---|
| 2003/0113937 | A1* | 6/2003 | Kipke | G01N 1/40 436/175 |
| 2014/0120537 | A1* | 5/2014 | Chang | B01L 3/502753 435/6.12 |
| 2017/0043914 | A1* | 2/2017 | Belfance | B65D 53/04 |

OTHER PUBLICATIONS

Thomas AC, Howard J, Nguyen PL, Seimon TA, Goldberg CS. ANDe™: A fully integrated environmental DNA sampling system. Methods Ecol Evol. 2018;9:1379-1385. https://doi.org/10.1111/2041-210X.12994.

* cited by examiner

SELF-PRESERVING BIODEGRADABLE ENVIRONMENTAL DNA FILTER

CROSS REFERENCES TO RELATED APPLICATIONS

This application claims the benefit of U.S. Provisional Patent Application No. 62/800,248, filed 1 Feb. 2019, entitled as "A SELF-PRESERVING BIODEGRADABLE ENVIRONMENTAL DNA FILTER", which is incorporated herein by reference in its entirety; this application is a continuation-in-art application of U.S. Utility application Ser. No. 15/678,964 entitled "Dynamic Environmental Water Sampling backpack" filed on Aug. 16, 2017, which further claims the benefit of U.S. Provisional Patent Application No. 62/375,886, filed Aug. 16, 2016, entitled as "Dynamic Environmental Water Sampling Backpack", which is incorporated herein by reference in its entirety.

FIELD OF THE INVENTION

The invention relates to an apparatus, systems and methods for the filtering and preserving of environmental DNA.

BACKGROUND

Field sampled environmental DNA from lakes, streams, and oceans is used to both identify the species that are present in the body of water and try to quantify the population of individual species. The technique of analyzing field sampled environmental DNA involves the field collection of aqueous samples from water bodies (streams, lakes, swamps, effluent discharges, etc.) and then testing those samples using DNA replication protocols.

DNA samples are subject to degradation when they are extracted for sampling. This degradation can be due to enzyme activity and/or chemicals that are added to the sample. During sampling, it is important to prepare and preserve samples in the field easily, quickly, and efficiently, so samples that are analyzed for environmental DNA are viable.

Some of the current protocols for the collection of field sampled environmental DNA involve the preparation and assembly of a sampling apparatus from separate components. One of the current drawbacks of field sampling methods is that the sampling of DNA using environmental DNA filters must be preserved to maintain the viability of the DNA samples. Preservation of the filters can involve transferring the filters to a chemical preservative, be desiccated, or require cold storage in the field. In one method the field preservation of DNA involves the field sampling technician opening up the filter cartridge; folding the environmental DNA filter with a pair of sterile forceps; then inserting of the filter into a vial or bag containing DNA preservative. These transfer steps can be challenging to perform by a field technician and there is an increased risk of sample contamination by inadvertent DNA contamination. Some field sampled environmental DNA technicians use fully encapsulated filters and then place the full filter cartridge in cold storage to preserve the DNA samples. However, transport of cold storage materials into the field may be costly or logistically prohibitive.

As the number of practitioners using environmental DNA survey methods has increased rapidly in recent years, the standards for what is considered acceptable environmental DNA practice have also increased. More emphasis is being placed on a rigorous set of lab and field protocols that minimize the potential for DNA contamination from myriad potential sources. New tools are therefore needed to help environmental DNA practitioners achieve these high standards both efficiently and cost-effectively. There is an indication that self-preserving environmental DNA filter cartridges are a viable alternative to standard environmental DNA preservation methods that help to reduce the risk of sample contamination, minimize protocol steps, and result in less plastic waste.

Therefore, there is a need to improve the preservation of field environmental DNA samples at the point of sampling in the field by the use of a desiccating filter cartridge.

BRIEF SUMMARY OF THE INVENTION

It is an object of this invention to provide an inline filter cartridge assembly having a hydrophilic and desiccating part, that when used in conjunction with a water suction system can function to both concentrate environmental DNA particulates from water samples and allow for the automatic preservation of the captured environmental DNA via desiccation, thus eliminating the requirement of filter membrane transfer steps, chemicals or cold storage requirements in the field.

It is also an object of this invention to provide a self-preserving environmental DNA filter cartridge that is made of hydrophilic plastic which desiccates an environmental DNA filter sample after collection where that hydrophilic plastic is an integrated component of the collection cartridges.

It is also an object of this invention to provide a hydrophilic plastic capable of absorbing any remaining moisture in the package and assisting in the preservation of the environmental DNA that is filtrated on the filter membrane at ambient field temperature.

It is also object of this invention to configure a filter cartridge assembly with a cartridge capable of improved access using a pull-tab mechanism and the filter membrane removed for sampled environmental DNA extraction in the laboratory to reduce the risk of contamination.

It is also an object of this invention to provide a process for collecting one or more field samples and to transport them to labs, without the necessity of cold storage materials or ethanol vials.

Further it is an object of this invention to provide a self-preserving filter that works with an environmental DNA pump system that reduces the potential for contamination by minimizing high-risk filter handling steps in the field. This was driven by an identified need for robust sampling protocols to improve environmental DNA data quality to the point where species detections via environmental DNA can be trusted and integrated into management or regulatory frameworks. Current field preservation methods often require filter membrane manipulations with sterile forceps that are difficult for even well-trained field staff to conduct reliably. Although rarely reported in the literature, these challenging steps can lead to filters being dropped or mishandled in the process of transfer to preservation media. The self-preserving (desiccating) filters described herein remove the membrane transfer steps altogether from the field protocol, which also improves the time efficiency of field staff tasked with collecting many samples in remote locations. Such improvements to the environmental DNA field sampling process are especially important given that many research studies now rely on citizen scientists and those who are not professionally trained to collect field samples.

Further it is an object of this invention to provide a partially biodegradable filter to help reduce the ecological impacts of environmental DNA sampling that generally relies heavily on single-use plastic components. Single-use consumables are often preferred by environmental DNA researchers because existing sterilization methods (i.e., bleach) can lead to false-positives when sterilization is insufficient, or false-negatives when residual bleach is carried over to subsequent samples. The self-preserving filters cartridges are currently designed to be a single-use sampling implement that is 50% comprised of a biodegradable plastic. This non-toxic material slowly dissolves when exposed to water for prolonged periods and then further breaks down in solution via microbial action.

The foregoing is not intended to be an exhaustive list of embodiments and features of the present inventive subject matter. Persons skilled in the art are capable of appreciating other embodiments and features from the following detailed description in conjunction with the drawings.

DETAILED DESCRIPTION

Figure 1:
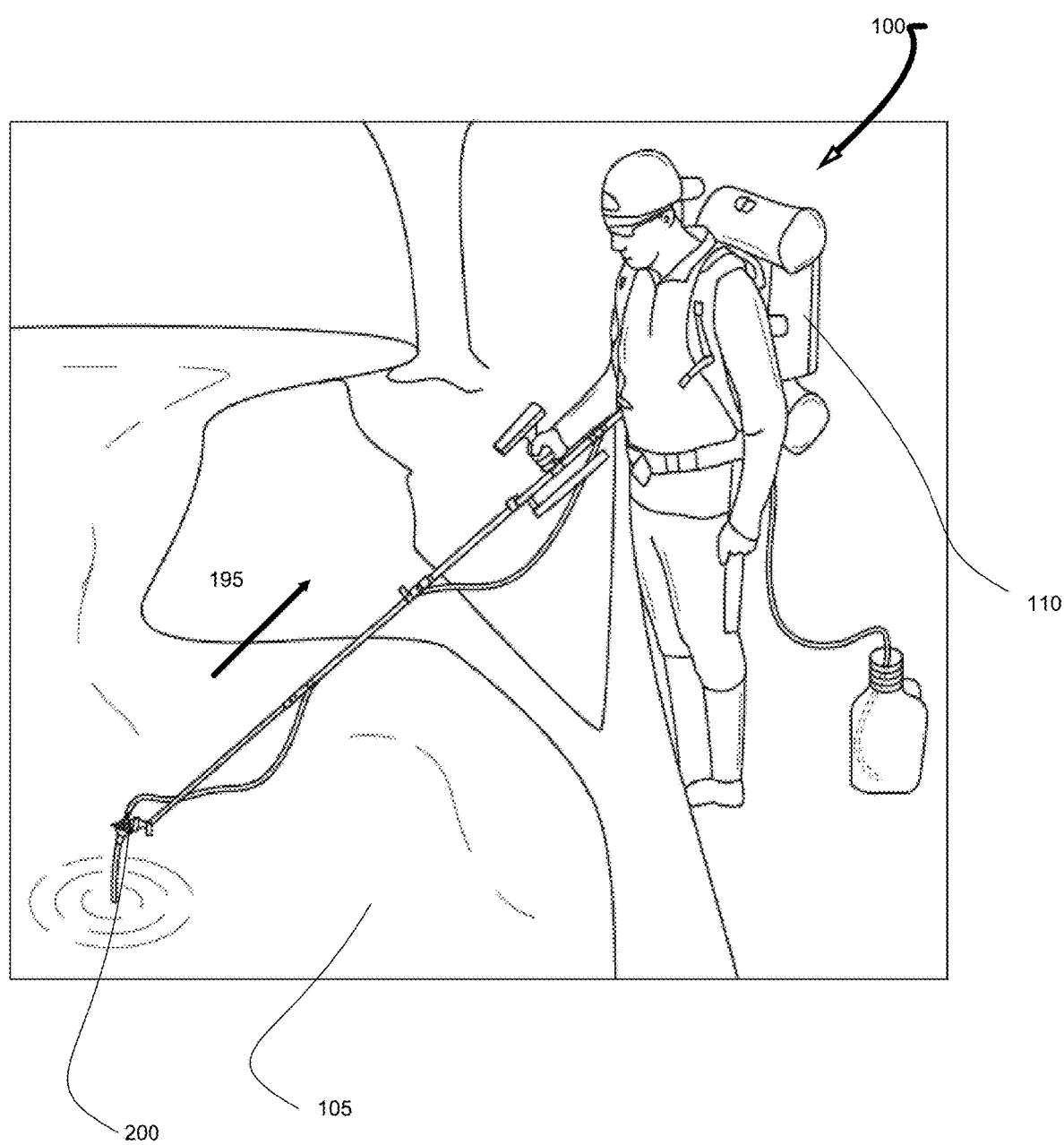
FIG. 1 is the sampling system for the collection of environmental DNA.

Now referring to FIG. 1 which illustrates the environmental DNA collection system 100. The sampling backpack 110 is used to draw water 105 through a filter cartridge assembly 200. The flow of the water 195, is from the body of water, through for this example, the Smith-Root eDNA backpack sampling system is depicted in this application, but alternate configurations where the sampling system is not configured as a backpack would be suitable, such as the sampling system could be mounted in a mobile case, a cart, or located inside a laboratory building. In this particular implementation, the water containing the environmental DNA is drawn upwards through the filter cartridge assembly 200 and then to the sampling backpack 110.

Figure 2:
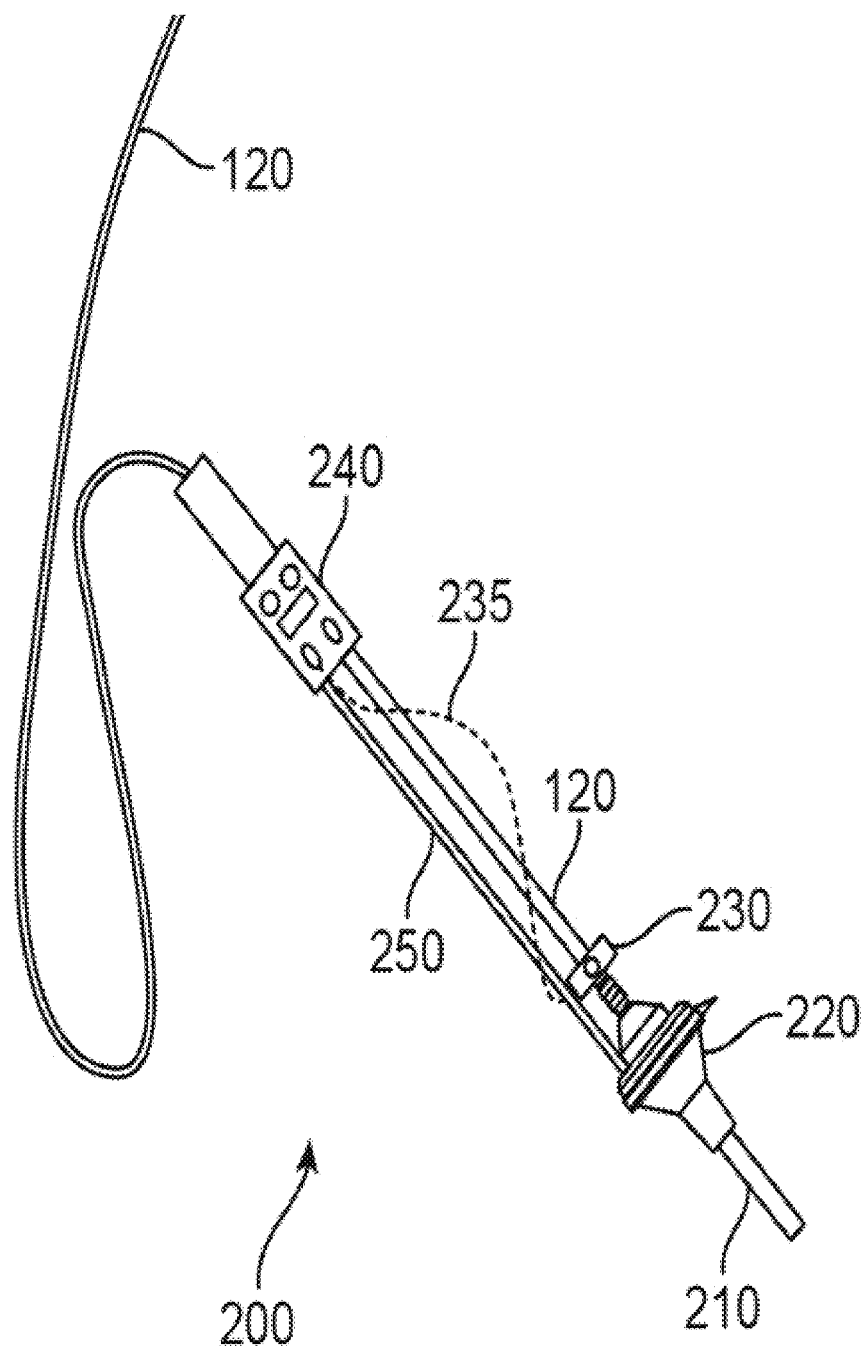
FIG. 2 is a close-up view of the sampling pole that holds the filter assembly cartridge.

Now referring to FIG. 2 which is the probe assembly which holds the filter cartridge assembly 220. The probe assembly aids in sampling by a placing the filter cartridge assembly 220 close to the body of water. Now referring to FIG. 2 which depicts the inventive subject matter of the water collection and filtration module 200, consisting of the induction tube 210, the filter cartridge assembly 220 and the pump tubing 120. In some embodiments, the flow rate sensor 230 may be located inside the casing for power and control module 100. The induction tube 210 draws water from the sampling source, using the suction generated by the pump, and directs the water into the filter cartridge assembly 220. Water flows through the filter cartridge assembly 220, where particulate is captured, and then flows into the pump tubing 120.

In the preferred embodiment, the amount of water drawn through the filter cartridge assembly 220 has a minimum flow rate of 0.1 L/min to a maximum flow rate of 1.4 L/min. The accuracy of fluid volume measurement is approximately greater than 90% at a rate of 0.1 L/min. The preferred orifice size is approximately 0.25 inner diameter tubing.

Figure 3:
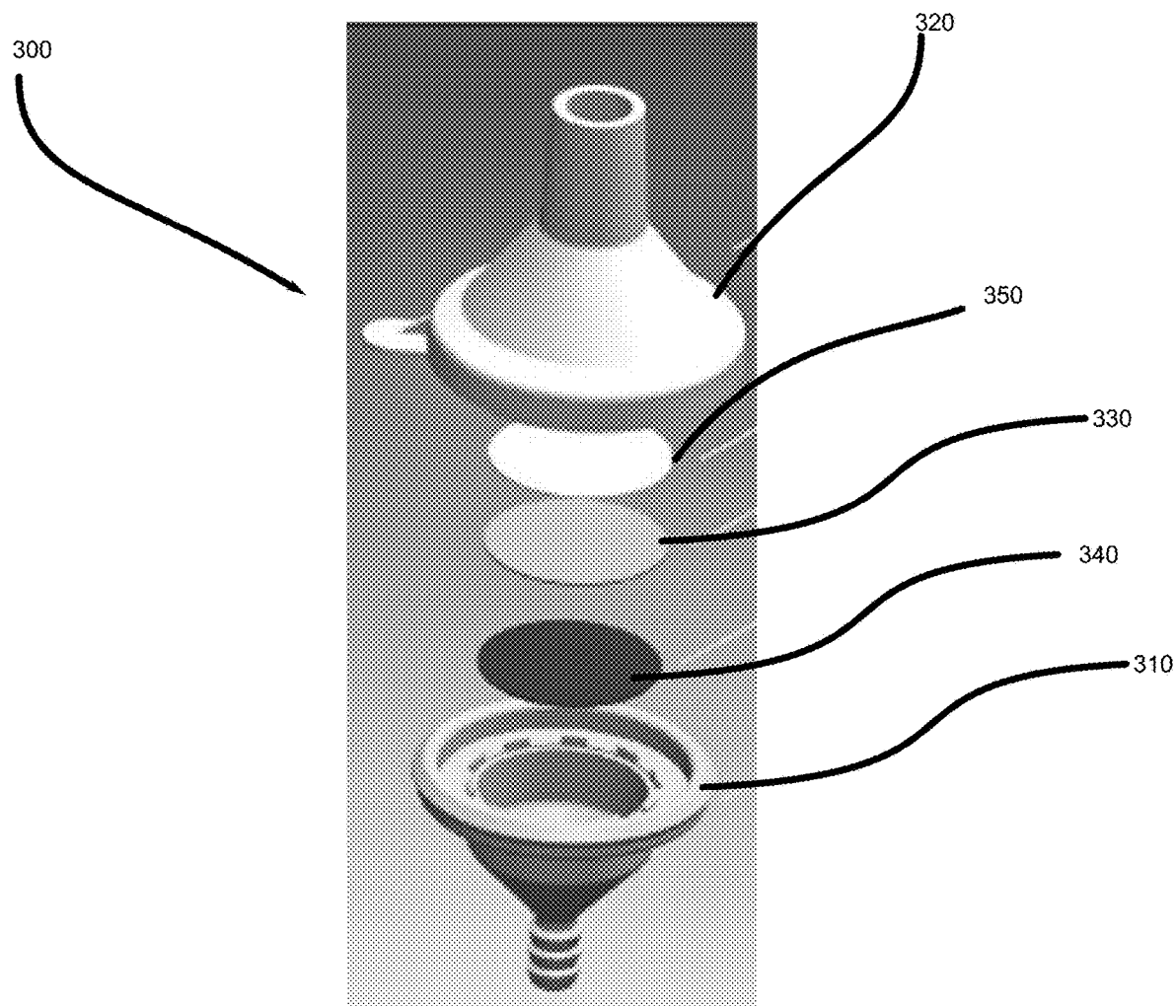
FIG. 3 is an exploded side view of the filter assembly cartridge.

Now referring the FIG. 3 which has an exploded view of the filter cartridge assembly 220 having a top 320, a filter membrane 350, a filter backer 330, a steel mesh 340, and a desiccating bottom 310. The water flows 195 through the top 320, through the filter membrane 350, the filter backer 330, the steel mesh 340, and out the desiccating bottom 310.

The filter membrane 350 should have a pore size that provides for the capture of environmental DNA but allows for the free passage of the liquid part of the sample. The filter membrane for sampling environmental DNA should range from 0.22 um (microns) to 40.0 um (microns).

The desiccating bottom 310 will be a hydrophilic material that is active at a range of field and laboratory temperatures (1-43 degrees Celsius) and capable of rapidly absorbing moisture from the filter membrane 350 encased in the filter cartridge. The filter membrane 350 materials can be Cellulose Acetate, Glass Fiber, MCE (Mixed Cellulose Ester), Nitrocellulose, Nylon, PCTE (Polycarbonate track etch), PES (Polyethersulfone), PETE (Polyester track etch), PAN (Polyacrylonitrile), PEEK (Polyether Ether Ketone), PVDF (Polyvinylidene fluoride)

Figure 4A:
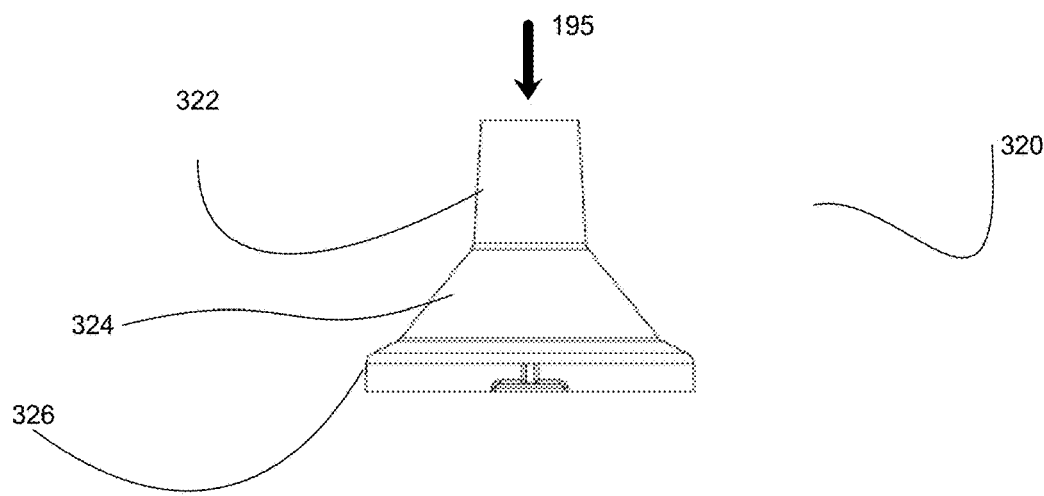
FIGS. 4A, 4B, and 4C are views of the top of the filter assembly cartridge.
Figure 4B:
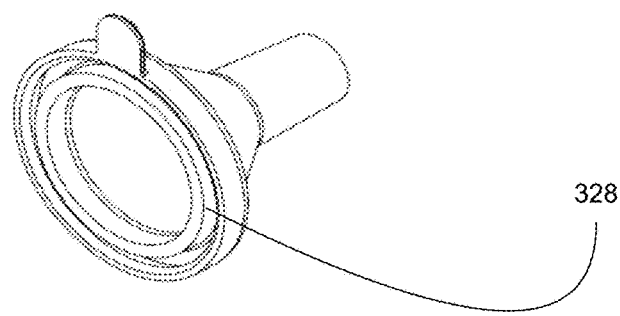
Figure 4C:
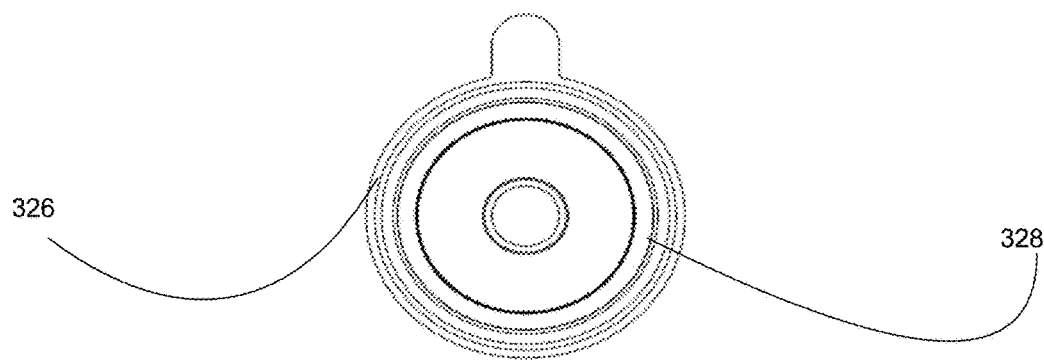

Now referring to FIGS. 4A, 4B, and 4C illustrating various orientations of the top 320. The top 320 has a tubular section 322 that allows the passage of liquids with an inlet port, the tubular section 322 is connected to a flared conical section 324, that terminates in a flexible lip structure 326. An embodiment of the top 320 closely resembles a funnel-like structure, but any corresponding structure is permissible, including, but not limited to cylindrical configurations, rectangular, cubicle, or other configurations. The flexible lip structure 326 with the flexible lip structure 326 has an inner mating ring 328 allows for a compression fit to the desiccating bottom 310. The top 320 may be made of any substance that is inert and does not contaminate the flow of water 195 or degrade DNA. While a flexible lip structure 326 is preferred, other coupling configurations that provide a seal are permissible, such as, inflexible compression fit, threaded couplings, or other similar couplings that allows passage of water without leakage.

Figure 5A:
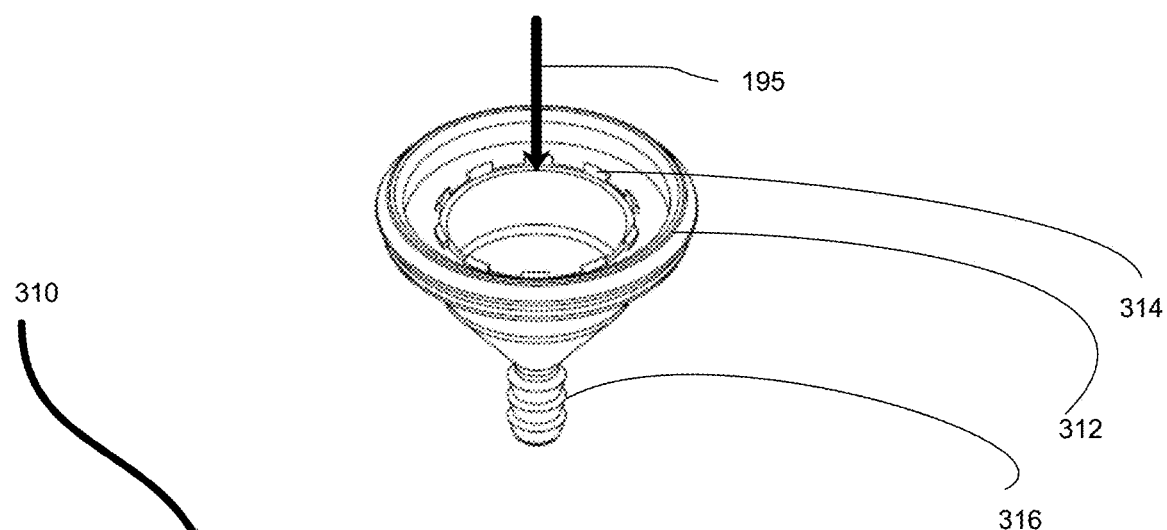
FIGS. 5A, 5B, and 5C are views of the desiccating bottom of the filter assembly cartridge.
Figure 5B:
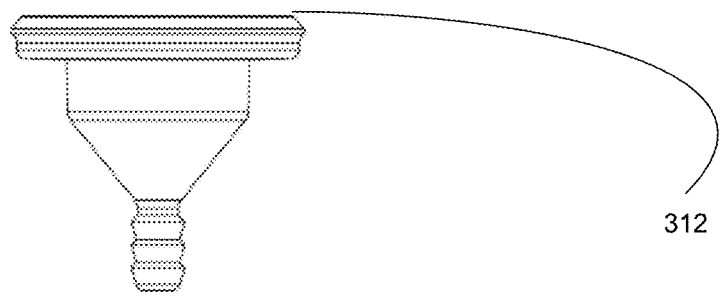
Figure 5C:
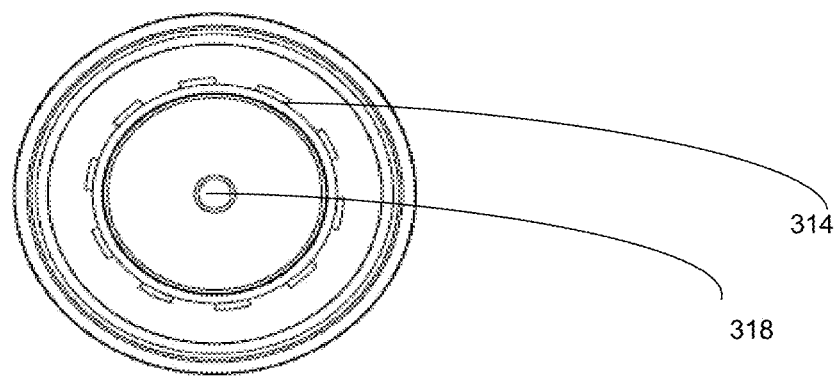

Now referring to FIGS. 5A, 5B, and 5C illustrating various orientations of the desiccating bottom 310. The desiccating bottom 310 has a tubular section 316 that allows the passage of liquids with an out of the outlet port, the tubular section 316 is connected to a flared conical section, that terminates in a ridged lip structure 312. An embodiment of the desiccating bottom 310 closely resembles a funnel-like structure, but any corresponding structure is permissible, including, but not limited to cylindrical configurations, rectangular, cubicle, or other configurations. The ridged lip structure 312 allows for a compression fit to the top 320. The top 320 may be made of any substance that is inert and does not contaminate the flow of water 195 or degrade DNA. While a ridged lip structure 312 is preferred, other coupling configurations that provide a seal are permissible, such as, inflexible compression fit, threaded couplings, or other similar couplings that all passage of water without leakage.

Now referring back to FIG. 3 and further in reference to FIG. 4 and FIG. 5. During operation, the filter cartridge assembly 220 draws water through the induction tube 210, through the filter membrane 350, a filter backer 330, a steel mesh 340, and then to the pump tubing 210. Environmental DNA is captured on the filter membrane 350. The bottom 310 of the filter cartridge assembly 220 is made of a hydrophilic substance that absorbs water. This absorption of water assists in the desiccating the filter membrane after sampling and preserves the membrane for subsequent DNA PCR analysis.

The filter membrane 350 may be dimensioned to any size, although use of an approximately 47 mm diameter is preferred.

Figure 7:
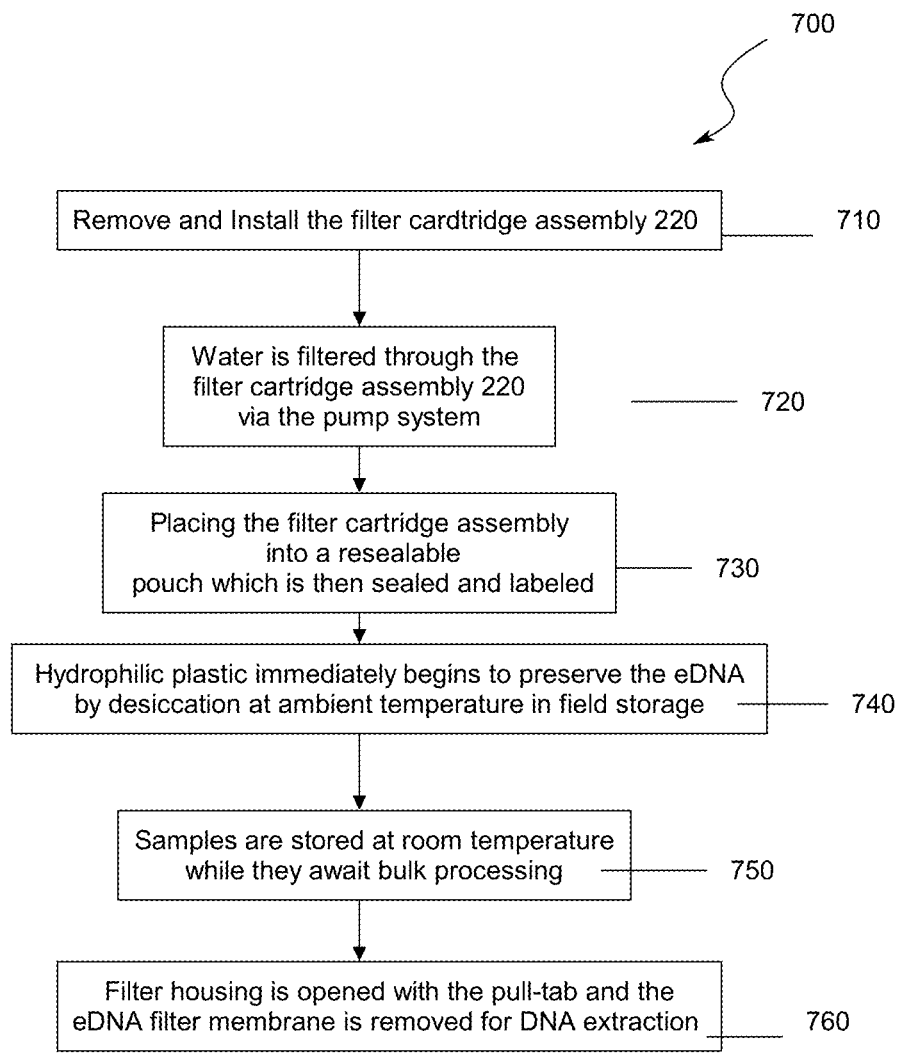
FIG. 7 shows a method for using the filter assembly cartridge.
Figure 8:
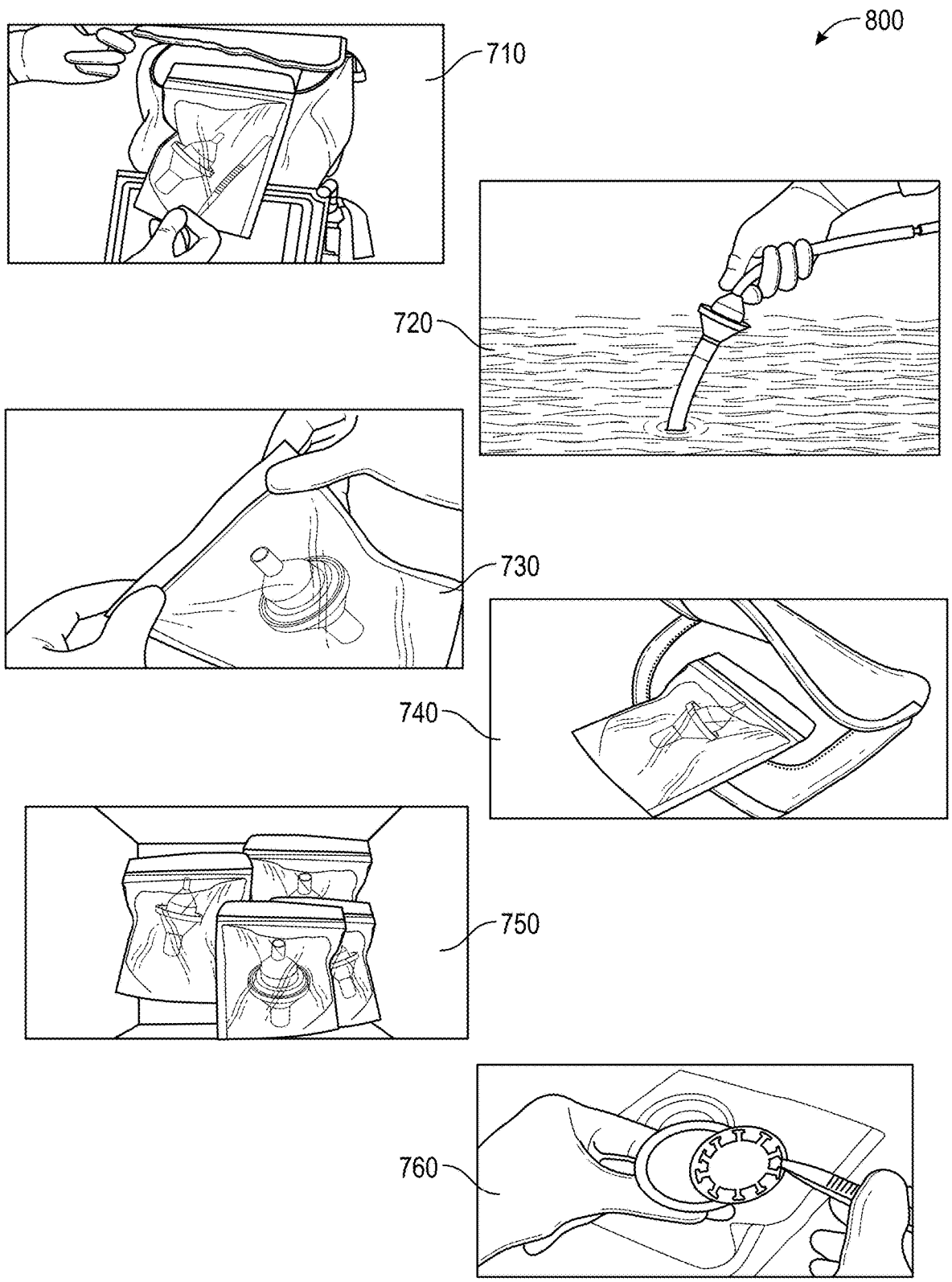
FIG. 8 shows a pictorial diagram of some of the steps in using the filter assembly cartridge.

Now referring to FIG. 7 (flowchart) and FIG. 8 (diagrammatic representation), which illustrates the method of installing and using the self-preserving environmental DNA filter cartridge assembly 220. A filter cartridge assembly storage packet is opened 710 containing the filter cartridge assembly 220 and induction tube 210. A water sample is collected from a water body and filtered 720 through the filter cartridge assembly 220 using the attachment to a pump system as illustrated in 200 of FIG. 2.

The filter cartridge assembly 220 is removed from the pump system placed unopened back into the resealable pouch 730 which is then sealed 730. Upon storage, the hydrophilic plastic immediately begins to preserve the environmental DNA by desiccation at ambient temperature 740. The field cartridge assembly may be stored at room temperature while they await bulk processing 750. The filter cartridge assembly 220 is opened by separating the top 320 from the desiccating bottom 310 and removing the filter membrane 350 for DNA extraction and analysis.

Use of the Filter Cartridge Assembly with Other Sampling Systems

The filter cartridge assembly 220 is not limited to only being used with the field sampling system described above. The filter cartridge assembly 220 may be used with any field sampling apparatus that will draw an environmental sample through a tube. The inlet and outlet ports of the filter cartridge assembly 200 may also be mated to other field sampling systems by using simply tube adapters on either the inlet or outlet ports.

Methods for the Preservation of the Field Sampled Environmental DNA

The steps for preserving the environmental DNA are shown in flow chart 700 for a self-preserving environmental DNA filter process with reference to the pictorial diagram 800:

A filter packet is opened containing the pre-loaded inline filter cartridge made with hydrophilic bottom 310.

The extension tube (in packet) and suction tubing are attached to the filter cartridge; pump is activated to begin filtration.

The suction tubing is then placed in the body of water (lake, stream, etc.).

Water is then filtered through the filter membrane by attachment to a pump system.

The filter cartridge is placed into a resealable pouch which is then sealed and labeled.

The hydrophilic plastic immediately begins to preserve the environmental DNA by desiccation at ambient temperature.

The filter cartridge is opened with the pull-tab and the environmental DNA filter membrane is removed for DNA extraction 260.

Another embodiment may also be employed:

Sample packet containing a filter cartridge assembly is removed from seal packet.

The extension tube (in packet) and suction tubing are attached to filter cartridge; pump is activated to begin filtration.

When "low flow" alarm sounds or target volume is reached, the filter cartridge is inverted and elevated to filter all remaining water in cartridge and clear the suction line.

Seal is cracked (not opened) and the pump continues to run for approximately 20 seconds to air dry the filter membrane.

The extension tube is removed from the filter cartridge and discarded.

The self-preserving filter cartridge is placed back into the original packaging.

The package is resealed, and the filter cartridge material immediately begins preserving the captured DNA via desiccation.

The sample is labeled and placed back inside field storage at ambient temperature.

Once in the laboratory, the technician removes the filter cartridge with preserved filter membrane inside.

The filter cartridge is opened by the pull-tab, revealing the environmental DNA filter membrane.

The environmental DNA filter membrane is removed from the cartridge with sterile forceps for DNA extraction, and the filter backer remains in the cartridge. All elements other than the environmental DNA filter membrane are then discarded.

Validation and Testing of the Field Sampled Environmental DNA

Figure 6:
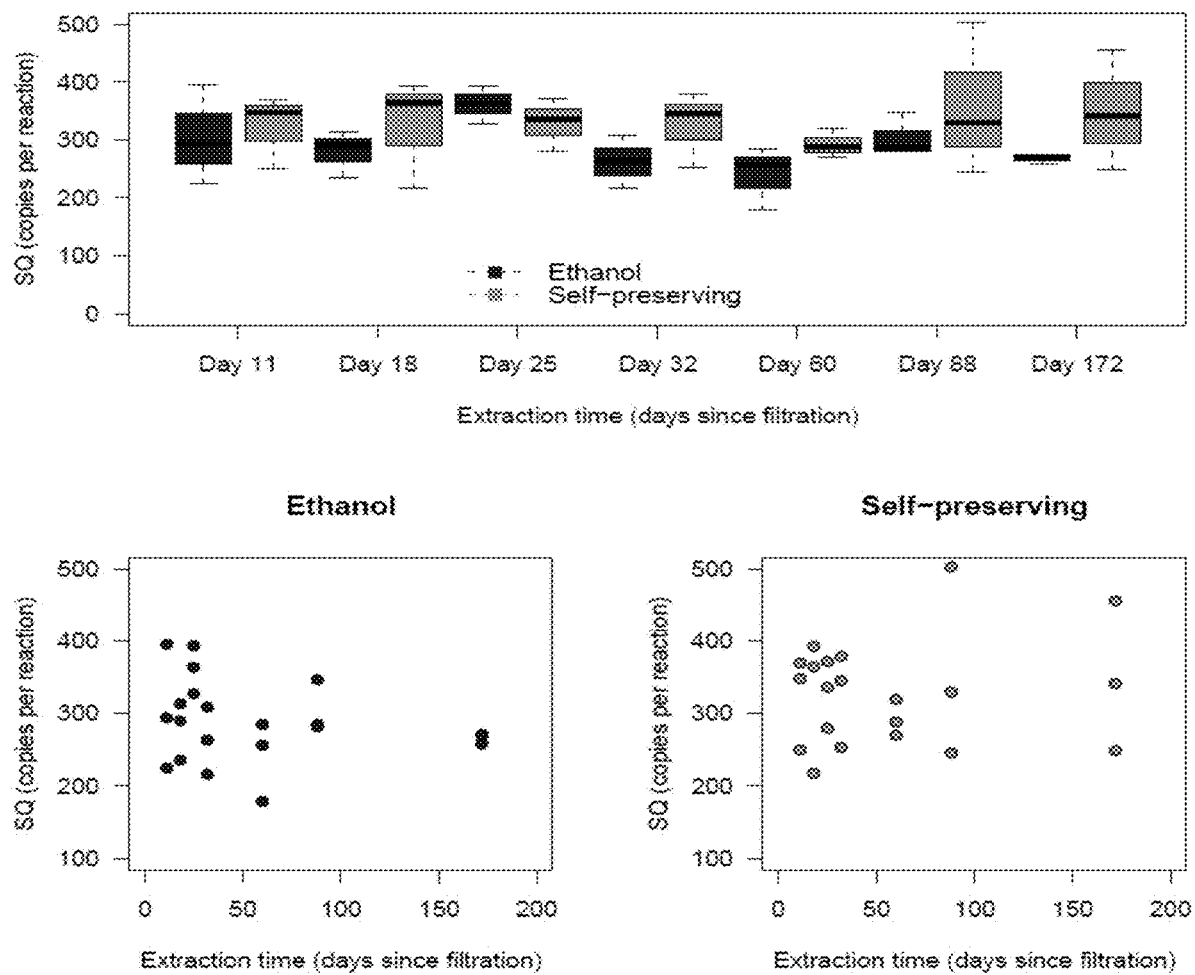
FIG. 6 depicts comparative test results

Now referring to FIG. 6, environmental DNA preservation capabilities of the hydrophilic filter cartridges were compared to the standard ethanol field preservation method using a mesocosm experiment. Replicate water samples were collected and filtered from a tank containing a single suspended concentration of New Zealand mudsnail (*Potamopyrgus antipodarum*) environmental DNA in river water. Half of the samples were preserved in ethanol and the other half were allowed to be self-preserved by placing the filter cartridge back in original packaging. The mudsnail environmental DNA preserved on filters was then extracted at multiple time points and quantified by qPCR to determine the degree of environmental DNA degradation over time for each preservation method.

A description of the materials and methods involved in the Mesocosm setup is as follows: A total of 88 L of environmental water was collected from a local creek and transferred to a 151 L total-volume test tank (91 cm L×46 cm W×21 cm H) held in a wet lab. Environmental water from the creek was used to ensure that the experiment accounted for naturally-occurring environmental PCR inhibitors. An additional 17 L of water from a rearing tank containing a small population of New Zealand mudsnails (~100 individuals) was added to the test tank to create a total volume of 105 L of water with known New Zealand mudsnail environmental DNA. Water in the test tank was circulated throughout the experiment using a gyre pump (Maxspect XF250-5300 GPH)—this ensured that New Zealand mudsnail environmental DNA was kept suspended and mixed throughout the tank. Detectability of New Zealand mudsnail environmental DNA was confirmed in the test tank prior to replicate sample collection by testing with Biomeme handheld qPCR.

A description of the water filtration and preservation is as follows: Water was filtered from the test tank using the Smith-Root environmental DNA sampler with single-use filter packets. The filter cartridges, contained in packets were pre-loaded with 1.0 μm (47 mm diameter) polyether sulfone (PES) filter membranes, that are 50% comprised of an injection-molded hydrophilic plastic. Filtration parameters on the environmental DNA sampler were standardized for all samples at 1.0 L/min flow rate, 13 psi pressure threshold, and 0.5 L target volume. Environmental DNA Filter samples were collected for both preservation treatments (ethanol, self-preserved) and labeled for DNA extraction at 7 time points post-collection: 11 days, 18 days, 25 days, 32 days, 60 days, 88 days, 172 days. Three replicate filter samples were collected for each combination of preservation method and extraction time point, for a total of 42 samples (21 ethanol, 21 self-preserved).

After filtration, the filter membranes for ethanol preservation were immediately removed from the cartridge, folded, and inserted into individual 2 mL test tubes filled with approximately 1.25 mL of 200 proof reagent-grade ethanol to sufficiently cover the sample. The sampling and preservation procedure for the self-preserved filters were modified to minimize the amount of moisture that the hydrophilic plastic was required to absorb. At the end of a filtration cycle the environmental DNA sampler produces an audible "low-flow" alarm—indicating that all water in the suction tubing has been metered and filtration is complete. For the self-preserved samples in this experiment, the pump was allowed to continue running for 20 seconds at this stage to effectively air dry the filter membrane. After the drying step the filter cartridge was placed back into the foil pouch and resealed using the zip-type sealing strip for preservation.

A description of the environmental DNA quantification and analysis is as follows: Samples of both preservation treatments were shipped overnight to the Goldberg lab at Washington State University and stored at room temperature until their prescribed DNA extraction time point. DNA was extracted from filters following the laboratory's standard protocol: filter homogenization via QIAshredder (Qiagen, Inc.), DNA extraction with the DNeasy Blood & Tissue Kit (Qiagen, Inc.) and 100 ul elution. Mudsnail environmental DNA on each filter was detected and quantified by triplicate qPCR using a custom assay previously described in Goldberg et al. (2013): NZMS F-TGTTTCAAGTGTGCTGGTT-TAYA, NZMS Probe—6FAMCCTCGAC-CAATATGTAAAT-MGB, NZMS R—CAAATGGRGCTAGTTGATTCTTT, using PCR reactions with QuantiTect Multiplex PCR Mix (Qiagen, Inc.). Recommended duplexing concentrations were used (0.4 mM of each primer, and 0.2 mM of each probe) on a BioRad CFX96 and downsized to 10-mL reactions. Cycling was 15 min initial denature at 95 C, followed by 50 cycles of 94 C for 60 s and 60 C for 60 s. An exogenous internal positive control (Applied Biosystems) was included in each well as a test for inhibition. Reaction Starting Quantity (SQ) was calculated by a standard curve comprising 10, 100, 1000, and 10000 copies per well of gBlock standard (IDT, Inc.) and run with each plate of filter sample extracts.

Mudsnail environmental DNA degradation over the storage period was compared between the two preservation treatments and the five extraction time points using the SQ values produced by qPCR. First, the SQ values from the three qPCR replicates were average for each filter sample. A two-way ANOVA was then performed on the filter SQ values, using "preservation method" and "extraction time" as predictor variables. The base aov function in R (R Core Team 2014), treating preservation method as a factor with two levels and extraction time (in days) as a continuous integer variable. We tested for the simple main effects and for an interaction between the two variables.

A description of the results obtained is as follows: Over the course of the full 6-month eDNA preservation period, the average SQ value (copies per reaction±SD) was slightly higher for the self-preserved filters (329±72) than it was with the ethanol preserved samples (288±56) ($F1.38=4.050$, $p=0.051$; FIG. 3). We did not detect any effect of DNA extraction time (days since collection) on SQ values ($F1.38=0.008$, $p=0.930$) or evidence of an interaction between preservation method and extraction time point ($F1.38=1.149$, $p=0.290$).

The above experiments infers that there is no significant difference in the environmental DNA preservation capabilities of the self-preserving filter cartridges and the industry-standard ethanol preservation method. Surprisingly, the average SQ values from self-preserved filters were actually slightly higher than those from ethanol-preserved filters. We also did not detect any difference in template environmental DNA quantify on the replicate filters over the course of a six-month preservation trial involving storage at room temperature. This suggests that both methods are effective options for field preservation of environmental DNA captured on filter samples, and that samples of both preservation types can be stored at low cost for up to two months.

Now referring to FIG. 6, which illustrates average environmental DNA quantity (SQ) from replicate filter samples extracted at seven time points after filtration (11 days, 18 days, 25 days, 32 days, 60 days, 88 days, 172 days), and from two preservation treatments: ethanol (black), self-preserving (grey). The experiment compares target environmental DNA degradation between methods over the course of the preservation trial.

Persons skilled in the art will recognize that many modifications and variations are possible in the details, materials, and arrangements of the parts and actions which have been described and illustrated in order to explain the nature of this inventive concept and that such modifications and variations do not depart from the spirit and scope of the teachings and claims contained therein.

All patent and non-patent literature cited herein is hereby incorporated by reference in its entirety for all purposes.

We claim:

1. An assembly for the filtration of environmental DNA, comprising:
    a top having an inlet port;
    a desiccating bottom having an outlet port, the desiccating bottom configured to preserve the environmental DNA in a filter membrane by desiccation, the filter membrane having a porosity capable of filtering DNA from a passage of liquid, wherein the top and the desiccating bottom are coupled to one another to form an interior cavity, and wherein the filter membrane is placed in the inner cavity.

2. The assembly of claim 1, wherein the assembly is configured such that liquid can pass from the inlet port of the top through the filter membrane and out the outlet port of the desiccating bottom.

3. The assembly of claim 1, comprising a filter member, further comprised of a filter membrane, and a filter backer, each mounted proximate to a steel mesh and placed in the interior cavity.

4. The assembly of claim 1, wherein the top and the desiccating bottom each comprise an outer tubular member.

5. The assembly of claim 1, further comprising an induction tube coupled to the inlet port of the top, wherein the induction tube is configured to draw water from a sampling source.

6. The assembly of claim 1, further comprising a pump tubing coupled to the outlet port of the desiccating bottom, wherein the pump tubing is configured to be attached to a pump system.

7. The assembly of claim 1, wherein the top and the desiccating bottom each have a tubular section connected to a flared conical section.

8. The assembly of claim 7, wherein the flared conical section of the top comprises a flexible lip structure and an inner mating ring allowing for a compression fit to the desiccating bottom.

9. The assembly of claim 7, wherein the flared conical section of the desiccating bottom comprises a ridged lip structure allowing for a compression fit to the top.

10. The assembly of claim 1, wherein the top is made of a material that is inert to water and DNA.

11. The assembly of claim 1, wherein the desiccating bottom is made of a hydrophilic substance that absorbs water.

12. A method for the collection of an environmental DNA sample, comprising:
opening a filter packet containing a filter cartridge assembly, the filter cartridge assembly comprising a top, a desiccating bottom and a filter membrane for separating environmental DNA from a liquid;
connecting the filter cartridge assembly to a pump system;
drawing the liquid through the filter membrane for a period of time by using the pump system so as to capture a sufficient amount of the environmental DNA for analysis in the filter membrane;
using the desiccating bottom to preserve the environmental DNA in the filter membrane by desiccation; and
analyzing the environmental DNA sample.

13. The method of claim 12, further comprising:
removing the filter cartridge from the pump system; and
placing the unopened filter cartridge back into the filter packet, wherein the filter packet is resealable.

14. The method of claim 13, wherein the desiccating bottom further comprises:
a hydrophilic plastic, and
wherein upon storing the filter cartridge in the filter packet, the hydrophilic plastic begins to preserve the environmental DNA by desiccation at ambient temperatures.

15. The method of claim 13, further comprising:
storing the field cartridge assembly at room temperature, and
opening the filter cartridge assembly by
separating the top from the desiccating bottom and removing the filter membrane for DNA extraction and analysis.

16. The method of claim 12, further comprising:
when a low flow alarm sounds or a target volume is reached,
inverting and elevating the filter cartridge to filter any remaining liquid in the cartridge and clear of water the suction tubing attached to the filter cartridge.

17. An assembly for the filtration of environmental DNA, comprising:
a top made out of a material inert to water and DNA, where the top has an inlet port;
a desiccating bottom configured to preserve the environmental DNA in a filter membrane by desiccation made out of a hydrophilic material that absorbs water, where the desiccating bottom has an outlet port and is coupled to the top to form an interior cavity for a passage of liquid; the filtering membrane having a porosity capable of filtering DNA from the passage of liquid and placed in the inner cavity;
a filter backer mounted proximate to the filter membrane and placed in the interior cavity; and
a steel mesh mounted proximate to the filter membrane and placed in the interior cavity, wherein the assembly is configured such that that the liquid can pass from the inlet port of the top through the filter membrane, the filter backer, and the steel mesh, in that order, and out the outlet port of the desiccating bottom, wherein the top and the desiccating bottom each have a tubular section connected to a flared conical section, wherein the flared conical section of the top comprises a flexible lip structure and an inner mating ring allowing for a compression fit to the desiccating bottom, and wherein the flared conical section of the desiccating bottom comprises a ridged lip structure allowing for a compression fit to the top.

18. The assembly of claim 17, wherein the assembly further comprises a biodegradable plastic.

19. The assembly of claim 18, wherein the filter membrane has a pore size ranging from 0.22 microns to 40.0 microns.

20. An assembly for the filtration of environmental DNA comprising:
a filtering membrane having a porosity capable of filtering DNA from the passage of liquid;
a filter housing that contains a desiccating element for water removal from the membrane; and
a top and a desiccating bottom coupled to one another to form an interior cavity, the desiccating bottom configured to preserve the environmental DNA in the filtering membrane by desiccation;
wherein the filtering membrane is placed in the interior cavity so that the environmental DNA is retained on the filtering membrane.

* * * * *